(12) United States Patent
Lawson et al.

(10) Patent No.: US 9,877,880 B2
(45) Date of Patent: Jan. 30, 2018

(54) FASTENING MEMBER HAVING BONDED REINFORCING LAYER

(71) Applicant: The Procter & Gamble Company, Cincinnati, OH (US)

(72) Inventors: Michael Irwin Lawson, Fairfield, OH (US); Todd Leon Mansfield, Cincinnati, OH (US); Karen Elizabeth Staubach, Blue Ash, OH (US); Marcus Schönbeck, Versmold (DE)

(73) Assignee: The Procter & Gamble Company, Cincinnati, OH (US)

( * ) Notice: Subject to any disclaimer, the term of this patent is extended or adjusted under 35 U.S.C. 154(b) by 61 days.

(21) Appl. No.: 14/617,125

(22) Filed: Feb. 9, 2015

(65) Prior Publication Data

US 2015/0150735 A1    Jun. 4, 2015

Related U.S. Application Data

(63) Continuation of application No. 13/600,268, filed on Aug. 31, 2012, now Pat. No. 8,974,431.
(Continued)

(51) Int. Cl.
*A61F 13/56* (2006.01)
*A44B 18/00* (2006.01)
*A61F 13/62* (2006.01)

(52) U.S. Cl.
CPC ...... *A61F 13/5622* (2013.01); *A44B 18/0069* (2013.01); *A61F 13/5633* (2013.01); *A61F 13/62* (2013.01); *A61F 13/622* (2013.01); *A61F 13/625* (2013.01); *Y10T 24/2767* (2015.01); *Y10T 24/2775* (2015.01)

(58) Field of Classification Search
CPC .... A61F 13/5622; A61F 13/62; A61F 13/622; A61F 13/625; A44B 18/0015; A44B 18/0038; A44B 18/0046; A44B 18/0049; A44B 18/0061; A44B 18/008
See application file for complete search history.

(56) References Cited

U.S. PATENT DOCUMENTS

| 4,568,344 A | 2/1986 | Suzuki et al. |
| 4,854,984 A | 8/1989 | Ball et al. |

(Continued)

FOREIGN PATENT DOCUMENTS

| JP | H 10-5278 A | 1/1998 |
| JP | 2010-119738 A | 6/2010 |

OTHER PUBLICATIONS

PCT International Search report dated Oct. 24, 2012 (13 pages).

*Primary Examiner* — Lynne Anderson
(74) *Attorney, Agent, or Firm* — William E. Gallagher

(57) ABSTRACT

A fastening member having a reinforced region is disclosed. The fastening member may have a first layer formed of a nonwoven and a second layer at its reinforced region formed of either a polymeric film or another nonwoven, bonded to the first layer by a plurality of bond sites arranged in a pattern. The polymer(s) forming the fibers of the first layer and the polymer(s) forming the film or fibers of the second layer may be of like chemistry to enhance thermal bonding between the layers at the bond sites. The fastening member may be imparted with enhanced appearance and tear resistance attributes and may be suitable for use as a fastening member of a wearable article such as a disposable diaper.

12 Claims, 14 Drawing Sheets

Related U.S. Application Data

(60) Provisional application No. 61/529,369, filed on Aug. 31, 2011.

(56) References Cited

U.S. PATENT DOCUMENTS

| | | | |
|---|---|---|---|
| 4,919,738 | A | 4/1990 | Ball et al. |
| 5,143,679 | A | 9/1992 | Weber et al. |
| 5,156,793 | A | 10/1992 | Buell et al. |
| 5,167,897 | A | 12/1992 | Weber et al. |
| 6,030,373 | A | 2/2000 | VanGompel et al. |
| 6,051,094 | A | 4/2000 | Melbye et al. |
| 6,255,236 | B1 | 7/2001 | Cree et al. |
| 6,620,490 | B1 | 9/2003 | Malchow et al. |
| 6,663,612 | B2 | 12/2003 | Shingu et al. |
| 6,692,477 | B2 | 2/2004 | Gibbs |
| 6,713,159 | B1 | 3/2004 | Blenke et al. |
| 6,717,028 | B1 | 4/2004 | Oberstadt |
| 6,740,071 | B2 | 5/2004 | Gibbs |
| 6,837,961 | B2 | 1/2005 | Malchow et al. |
| 6,921,570 | B2 | 7/2005 | Belau et al. |
| 7,056,411 | B2 | 6/2006 | Desai et al. |
| 7,513,969 | B2 | 4/2009 | Ashraf |
| 7,662,278 | B2 | 2/2010 | Brooks et al. |
| 7,806,883 | B2 | 10/2010 | Fossum et al. |
| 7,862,549 | B2 | 1/2011 | Desai et al. |
| 7,870,652 | B2 | 1/2011 | Kline et al. |
| 8,158,849 | B2 | 4/2012 | Ashraf et al. |
| 8,177,766 | B2 | 5/2012 | Mansfield |
| 8,193,407 | B2 | 6/2012 | Mansfield |
| 8,226,626 | B2 | 7/2012 | Haines et al. |
| 8,337,479 | B2 | 12/2012 | Nilsson et al. |
| 8,974,431 | B2 * | 3/2015 | Lawson ............... A61F 13/62 604/389 |
| 9,241,847 | B2 | 1/2016 | Kline et al. |
| 9,241,848 | B2 | 1/2016 | Kline et al. |
| 9,375,362 | B2 | 6/2016 | Kline et al. |
| 2003/0091807 | A1 | 5/2003 | Desai et al. |
| 2003/0104748 | A1 | 6/2003 | Brown et al. |
| 2004/0222553 | A1 | 11/2004 | Desai et al. |
| 2006/0149209 | A1 * | 7/2006 | Malchow ............... A61F 13/49 604/389 |
| 2006/0287637 | A1 | 12/2006 | Lam et al. |
| 2007/0157441 | A1 * | 7/2007 | Kline ............... A44B 18/0069 24/442 |
| 2007/0254457 | A1 | 11/2007 | Ducauchuis et al. |
| 2008/0311338 | A1 | 12/2008 | Peterson et al. |
| 2009/0069772 | A1 | 3/2009 | Sauer et al. |
| 2009/0069774 | A1 | 3/2009 | Sauer et al. |
| 2009/0069775 | A1 | 3/2009 | Sauer et al. |
| 2009/0069777 | A1 | 3/2009 | Sauer et al. |
| 2009/0069778 | A1 | 3/2009 | Sauer et al. |
| 2009/0069779 | A1 | 3/2009 | Sauer et al. |
| 2009/0069781 | A1 | 3/2009 | Sauer et al. |
| 2009/0069782 | A1 | 3/2009 | Sauer et al. |
| 2010/0312207 | A1 | 12/2010 | Rexai et al. |
| 2011/0092946 | A1 | 4/2011 | Kline et al. |
| 2011/0092947 | A1 | 4/2011 | Kline et al. |
| 2012/0116342 | A1 | 5/2012 | Stjernholm et al. |
| 2016/0262959 | A1 | 9/2016 | Kline et al. |

* cited by examiner

FASTENING MEMBER HAVING BONDED REINFORCING LAYER

CROSS REFERENCE TO RELATED APPLICATION

This application is a continuation of U.S. application Ser. No. 13/600,268, filed Aug. 31, 2012, which claims the benefit of U.S. Provisional Application No. 61/529,369, filed Aug. 31, 2011, the substances of which are incorporated herein by reference.

BACKGROUND OF THE INVENTION

Nonwoven webs formed of fibrous materials ("nonwovens") and laminate webs formed of nonwovens laminated with other nonwovens and/or polymeric films, have been used as component materials in the manufacture of a number of products. Nonwovens such as those formed of polyethylene and/or polypropylene fibers can have cloth-like feel and mechanical strength characteristics, combined with desirable cost attributes, which make them useful in the manufacture of certain kinds of wearable articles. Thus, various types of polyethylene and/or polypropylene nonwovens are used in the manufacture of wearable articles such as disposable diapers.

In some examples of disposable diapers as well as other wearable articles, it may be desirable that a component web material be elastically extensible. Thus, a laminate web may be manufactured and include one or more layers of nonwoven to impart a cloth-like feel and/or mechanical strength attributes, and one or more elastomeric members, such as an elastomeric film layer, to impart elastic extensibility.

Some types of disposable baby diapers include side fastening members formed in part from a nonwoven and/or nonwoven laminate. In such examples, each of two fastening members may include an elastically extensible proximal portion attached to a rear waist region of the diaper, and a distal tab portion having an affixed fastener component such as a patch of hooks that constitutes a component of a hook-and-loop fastening system. Such an example may be designed to allow a caregiver who will apply the diaper to lay the diaper open on a surface and maneuver the rear waist region of the diaper to a suitable position beneath a reclining baby's bottom, wrap the front waist region of the diaper forward between the baby's legs and up over the front of the baby's lower torso, draw each fastening member from the rear waist region around a hip, and attach the distal portion of each fastening member to the front waist region via the fastener component, thereby forming a pant-like structure about the baby's lower torso. When such a fastening member includes a patch of hooks at its distal end, a front waist region of the diaper may include a landing zone, which may be a patch of material (the loop component) that is selected for its suitability for effective engagement by the hooks, and sufficient strength characteristics. Thus, upon engagement by the hooks with the landing zone, an attachment of the fastening member to the landing zone of sufficient strength to sustain forces resulting from the baby's movements, and satisfactorily hold the diaper on the baby, may be provided.

When in use, the configuration of fastening members of the exemplary type described above, as well as other members or components formed of nonwovens and/or laminates of nonwovens, may result in concentrations of forces and stresses in various portions thereof. For example, where a fastening member includes an extending tab portion formed of a separate material and bonded to a stretch laminate, and bears an affixed fastener component at a distal portion thereof, forces sustained and transferred through the fastener component may result in concentration of stresses in the material about bonds between the material forming the tab and the stretch laminate, and/or about the fastener component. In another example, a fastening member may taper or narrow from its proximal portion to its distal portion. Thus, when a caregiver tugs on the fastening member by its distal portion in order to apply the diaper to a baby, stresses may concentrate in the distal portion in areas of the material about the caregiver's grasp, or about a fastener component. Concentrations of stresses in materials in these examples, as well as in other examples, may in some in some circumstances be sufficient to initiate tearing or separation of materials. This may be undesirable because it may negatively affect the fit and/or performance of the product. It also may give rise to negative perceptions of quality on the part of the caregiver or other consumer.

In addition, fastening members having tabs of separate materials may be deemed in some circumstances to have an unsightly appearance, and may involve the added manufacturing steps required to affix tabs to stretch laminates.

Thus, in the interests of simplification, cost reduction, improved appearance and improved mechanical properties, alternative ways, for imparting needed features with added strength or reinforcement to fastening members, are desirable.

DETAILED DESCRIPTION OF THE INVENTION

Figure 1:
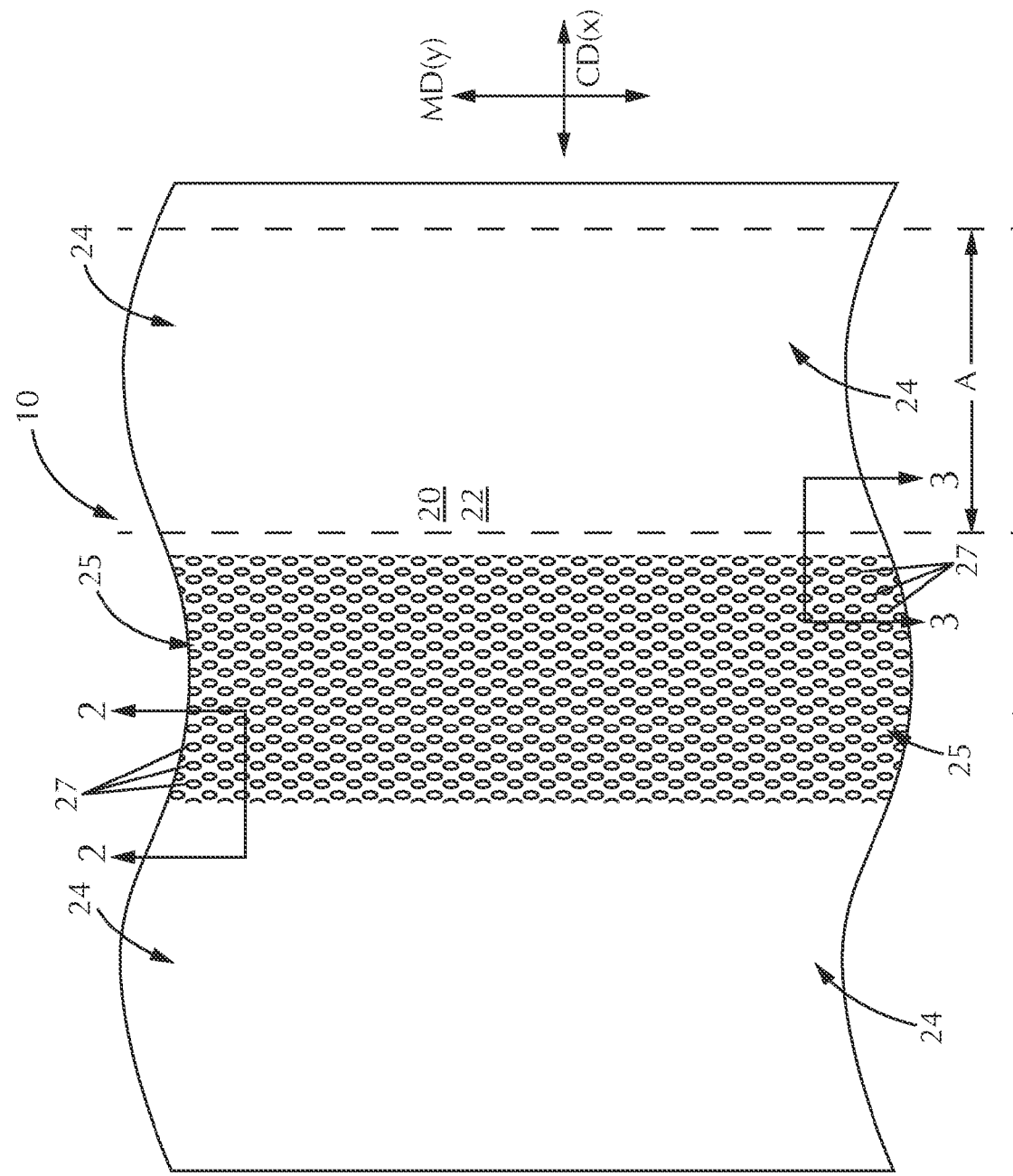
FIG. 1 is a schematic, plan view of a portion of a material web.

The "cross direction" of a web is the direction along the web that is perpendicular to its predominant direction of movement through processing machinery during its manufacture.

"Elastic" or "elastomeric" refers to the property of a material that elongates, without substantial rupture or breakage, by at least 50% at a load of between 0.1 and 10 N/cm in the Hysteresis Test. Rupture or breakage having a dimension less than 5 mm in any direction is not considered substantial rupture or breakage. However, ruptures through the structure having a dimension greater than 5 mm in any direction, breaks, ruptures or tears into two or more pieces, or breaks, ruptures or tears resulting in significant structural degradation which render the material unusable for its intended purpose, are considered substantial ruptures or breakage. Further, upon release of the load, the elastic material has a set less than or equal to 20% as measured according to the Hysteresis Test. For example, an elastic material that has an initial length of 25 millimeters can elongate to at least 37.5 millimeters (50% elongation) and, upon removal of the force, retract to a length of 27.5 millimeters, i.e., have a set of 2.5 millimeters (10% set), when subjected to the Hysteresis Test. It will be appreciated that this definition of elastic cannot be applied to materials such as individual elastic strands that do not have sufficient dimensions (e.g., not wide enough) to be properly subjected to the Hysteresis Test. As an alternative, such material is considered to be "elastic" if it can be elongated by at least 50% upon application of a biasing force, and return substantially to its original length (i.e., exhibit less than 20% set) upon release of the biasing force.

"Film" means a skin-like or membrane-like layer of material formed of one or more polymers, which does not have a form consisting predominately of a web-like structure of consolidated polymer fibers or other fibers.

"Lateral" and forms thereof when used in connection with a description of a diaper or components thereof, means extending along a direction generally or approximately parallel the waist edges.

"Like chemistry," with respect to two polymers, means that the two polymers are capable of mixing at a temperature of 250° C. or lower, to form a single thermodynamic phase.

"Longitudinal" and forms thereof when used in connection with a description of a diaper or components thereof, means extending along a direction generally or approximately perpendicular the waist edges.

The "machine direction" of a web is the direction along the web that is parallel to its predominant direction of movement through processing machinery during its manufacture.

"Machine direction orientation", with respect to the fibers forming a nonwoven component of a web, means that a majority of the fibers, as situated in the web and unstretched, have lengths with machine direction vector components that are greater than their cross direction vector components.

"Nonwoven" refers to a cloth-like web material formed of fibers that are neither knitted nor woven. Examples of nonwovens include but are not limited to web materials formed of polymer fibers formed and laid down through airlaying, wetlaying, spunbonding, meltblowing and bonded carded web processes, or combinations thereof, and calendered and at least partially bonded together by various processes and/or added bonding materials.

"Stiffness" of a portion of a web is measured according to the Stiffness Method herein.

"Tensile strength," with respect to a laminate web material, is the maximum tensile force per unit width of the material (width measured in a direction perpendicular to the tensile force direction) that the material will sustain before failure, measurable in a sample of the material having a uniform width.

"x-direction," with respect to a web, is the same as the cross direction.

"y-direction," with respect to a web, is the same as the machine direction.

"x-y plane," with respect to a web, refers to a plane substantially approximated by a macroscopic surface of the web laid out flat.

"z-direction," with respect to a web, refers to a direction perpendicular to an x-y plane.

Figure 2:
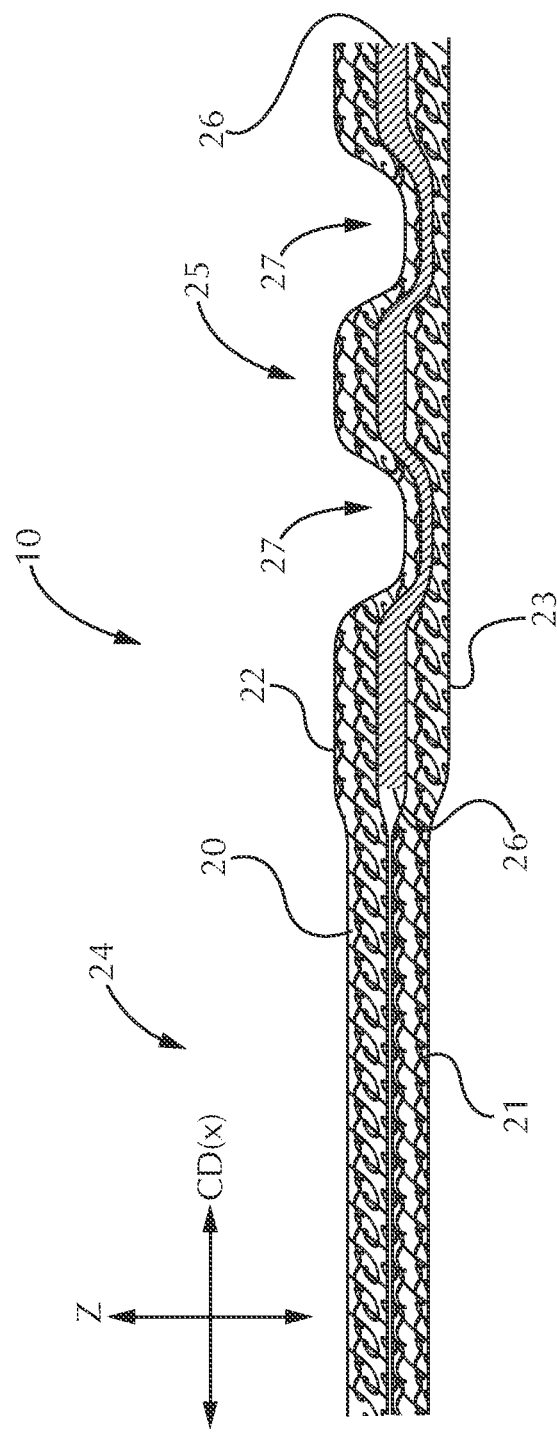
FIG. 2 is a schematic, cross-sectional view of a portion of a material web.

An example of a portion of a web having certain advantageous features is depicted schematically in FIGS. 1 and 2. FIG. 1 schematically depicts a portion of such web in plan view, while FIG. 2 schematically depicts a portion of such web in cross section.

Web 10 may include a first side 22, second side 23, and a first nonwoven layer 20, and may include a second nonwoven layer 21. First and second nonwoven layers 20, 21 may be a nonwoven of any suitable type, including a nonwoven formed of fibers of polyethylene, polypropylene, polyurethane, poly(ethylene terephthalate) and/or combinations thereof, formed into a material web by any of a number of processes for manufacturing nonwovens known in the art. The web 10 has a machine direction MD, a cross direction CD, and a Z direction.

Web 10 may also include first and second regions 24, 25. In first region 24, first and second nonwoven layers 20, 21 may be laminated directly together or with another layer using any suitable bonding means. The bonding means may be any suitable bonding means known in the art. For example, in some embodiments, at least one of the bonding means may be an adhesive. Any suitable adhesive can be used. For example, a suitable adhesive may be a styrene-olefin-styrene triblock copolymer such as styrene-isoprene-styrene, styrene-butadiene-styrene, the like, or combinations thereof. An example of a suitable bonding agent is an adhesive made available from Bostik, Wauwatosa, Wis. under the designation H2511.

In the second region 25, a polymeric film layer 26 may be included, and may be disposed between first and second nonwoven layers 20, 21. Polymeric film layer 26 may be formed of one or more polymers including polypropylene, polyethylene, poly(ethylene terephthalate), nylon, polyurethane or combinations thereof.

In some examples a layer of nonwoven may be used as layer 26. This nonwoven layer 26 may be formed of one or more polymers including polypropylene, polyethylene, poly (ethylene terephthalate), nylon or combinations thereof. Suitable fibers for forming a layer 26 of nonwoven may include natural and synthetic fibers as well as bicomponent, multicomponent, and shaped polymer fibers.

Layers including first nonwoven layer 20, polymeric film layer 26, and second nonwoven layer 21 may be bonded together at a plurality of bond sites 27. As may be appreciated from FIG. 2, bond sites 27 may be areas where the respective layers 20, 26, and 21 are compressed together. Bond sites 27 also may be areas where the respective layers 20, 26, and 21 are fused or welded together to some extent, such that the respective polymeric structures forming these layers (e.g., fibers, film, fibers) are partially or entirely visibly indistinct. A multi-layer structure may be formed in which the layers are held together at these bond sites 27. As may be appreciated from FIG. 1, bond sites 27 may have bond impressions that have shapes (for example, oval shapes as shown in FIG. 1), arranged in a pattern. Bond impressions at bond sites 27 may have any other shapes as well, including but not limited to circles, ellipses, rods, rectangles, triangles, diamonds, other polygons, rings, decorative shapes (such as hearts, flowers or other objects, smiley faces, stylized images of people, animals or anthropomorphic characters, popular cartoon or media characters, etc.), "H" shapes, "I" shapes, "L" shapes, "U" shapes, "V" shapes, "W" shapes, undulating paths, zigzag paths, "X" shapes and combinations thereof. Alternatively, bond impressions at bond sites 27 may constitute compressed areas which surround and define uncompressed, unbonded areas having shapes including but not limited to ovals, circles, ellipses, rods, rectangles, triangles, diamonds, other polygons, rings, decorative shapes (such as hearts, flowers or other objects, smiley faces, stylized images of people, animals or anthropomorphic characters, popular cartoon or media characters, etc.), "H" shapes, "I" shapes, "L" shapes, "U" shapes, "V" shapes, "W" shapes, undulating paths, zigzag paths, "X" shapes and combinations thereof.

Bond impressions at bond sites 27 need not be of uniform size, shape or rotational orientation within the x-y plane, but rather, may be varied in size, shape and/or rotational orientation. Bond sites 27 also may be disposed so as to form repeating patterns of such shapes. FIG. 1 depicts one example, in which bond impressions at bond sites 27 form a repeating pattern of oval shapes. The shapes may be aligned, or offset along one or both the machine direction and the cross direction. In the example depicted in FIG. 1, the repeating pattern of oval-shaped bond sites 27 may be spaced and/or offset along the machine direction, such that no line lies within second region 25 along the first side 22 of the web, parallel to the machine direction, and unoccupied by at least a portion of at least one of the bond sites 27. Similarly, a repeating pattern of bond sites may be suitably spaced and/or offset along the cross direction, such that no line lies within second region 25 along the first side 22 of the web, parallel with the cross direction, and unoccupied by a least a portion of at least one of the bond sites.

As may be seen in FIG. 2, bond sites 27 may comprise bond impressions in the web having a depth in the z-direction, where the layers have been compressed together in the z-direction. It may be desirable for these impressions to be present predominately or exclusively only on one side (such as first side 22) of the web, with the other side having a relatively flatter surface (such as second side 23), i.e., a surface that more closely approximates an x-y plane. The flatter surface may provide greater and more uniform surface area for adhesion, onto which additional materials or layers may be more effectively adhered or laminated. For example, it may be desirable that second side 23 be approximately flat as suggested, to provide greater and more uniform surface area for adhesion of a patch of hooks 40 (see FIGS. 3, 5) that may be provided as a fastening system component.

The presence of polymeric film layer 26 may impart second region 25 with a tensile strength and a stiffness in one or both the machine direction and cross direction that is greater than those of first region 24, thus providing reinforcing of the web 10 in second region 25. Further, without intending to be bound by theory, it is believed that an arrangement of bond sites 27 as described above prevents x-y direction movement of layers 20, 26, 21 with respect to each other, thereby further contributing to enhancement of stiffness in second region 25. If bond sites 27 are formed without the use/presence of an adhesive, the material cost of adhesive that otherwise may be required to laminate layers 20, 26, 21 is saved.

Figure 4:
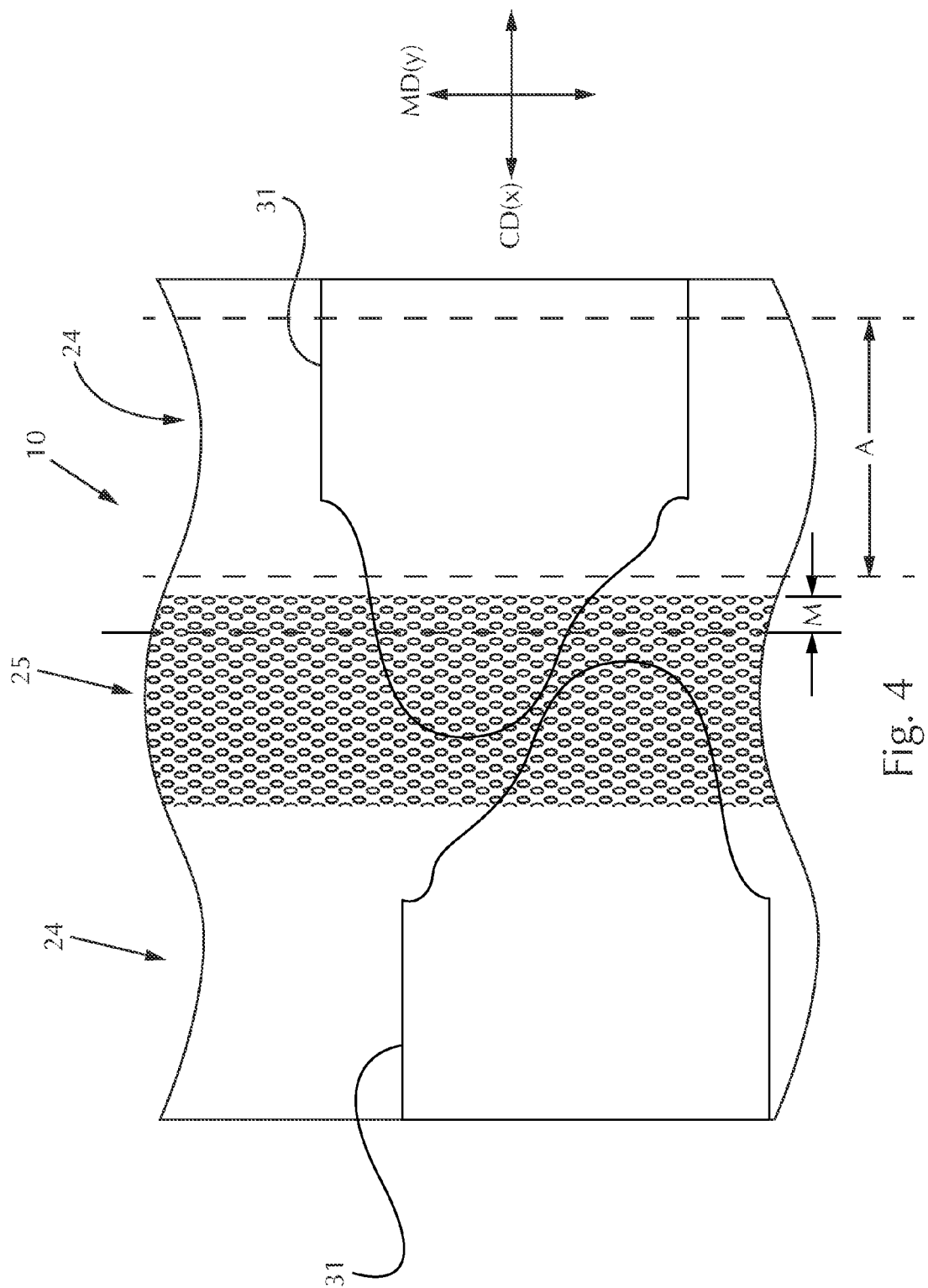
FIG. 4 is a schematic, plan view of a portion of a material web shown with cutout paths depicting an example of a way in which such a material web may be cut, to form fastening members.
Figure 5:
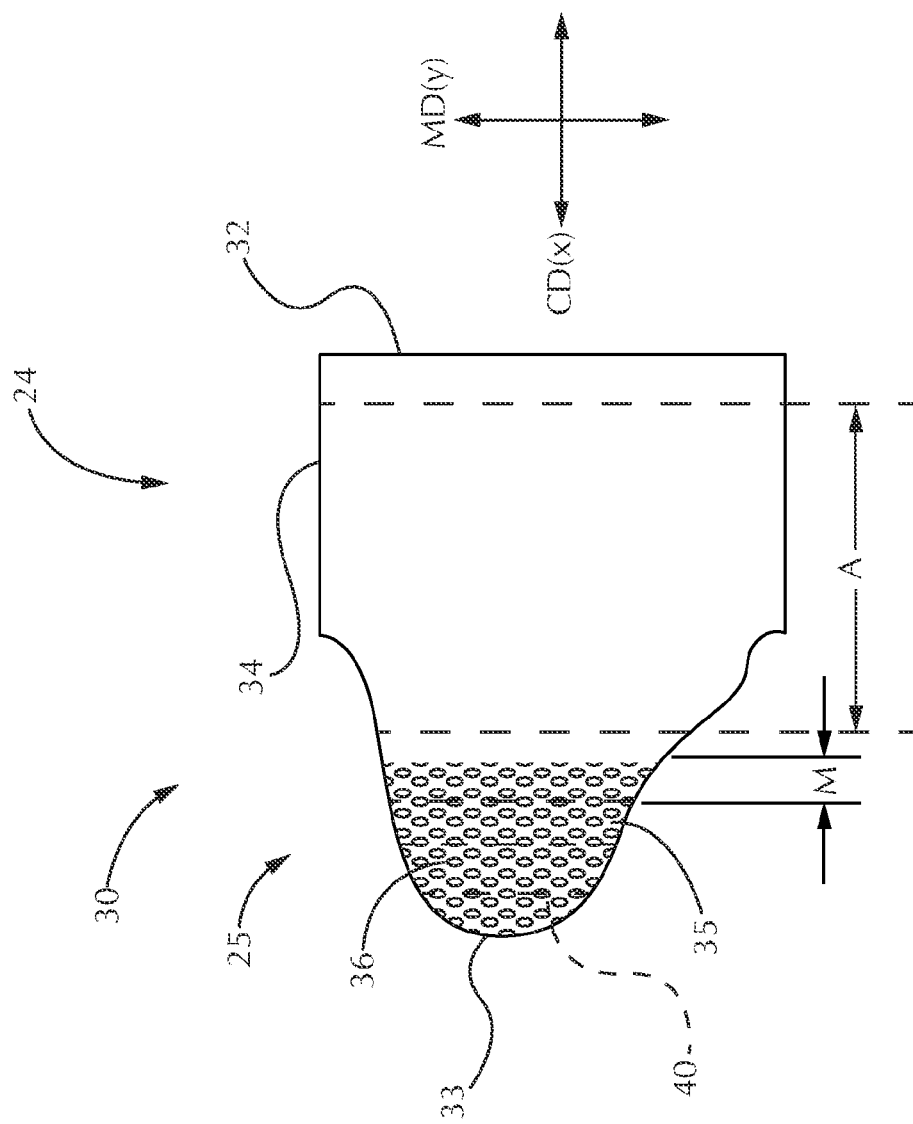
FIG. 5 is a schematic, plan view of a fastening member cut from the material web shown in FIG. 4.

Web 10 also may be provided with one or more additional members or layers of material for various purposes. Web 10 may include an elastomeric member extending in any direction such as one or more elastomeric strands, bands, strips, scrim, etc. For example, referring to FIG. 3, web 10 may include an elastomeric film layer 28 laminated between nonwoven layers 20, 21. Elastomeric film layer 28 may be formed of any elastomeric film suitable for the intended use of web 10, including, without limitation, elastomeric films disclosed in U.S. Published Application Nos. US 2007/0293111; US 2007/005038; US 2007/0167929; and US 2006/0244184; and U.S. Pat. Nos. 7,806,883; 7,862,549; and 7,513,969 the disclosures of which are incorporated herein by reference. For example, in applications where fastening members of diapers may be cut from web 10 (such as, for example, as depicted in FIGS. 4 and 5, discussed further below), elastomeric film layer 28 may be included to impart elastic extensibility to a portion of web 10, thereby providing for elastic extensibility of fastening members cut from web 10. Elastomeric film layer 28 may be adhered to nonwoven layers 20, 21 using any suitable adhesive and laminating equipment. An elastomeric film layer 28 may be bonded to film layer 26 in overlap margin M by a suitable adhesive.

A second nonwoven layer 21 may included, and may be a nonwoven of the same type as first nonwoven layer 20, or a different type, depending upon, among other factors, desired mechanical properties, feel, appearance and cost attributes. It may be desired to include second nonwoven layer 21 for purposes of added strength in either of first or second regions 24, 25; for purposes of providing a covering over elastomeric material layer 28 to impart a cloth-like feel (elastomeric film layer 28, if not covered, may have a rubbery or tacky feel); for purposes of covering and imparting a cloth-like feel or appearance over polymeric film layer 26; or for other purposes. Second nonwoven layer 21 may be adhered to the underlying material such as elastomeric film layer 28 and/or polymeric film layer 26 using any suitable adhesive and laminating equipment. Alternatively, in second region 25, second nonwoven layer 21 may be adhered to the laminate at bond sites 27, as described above.

Figure 3:
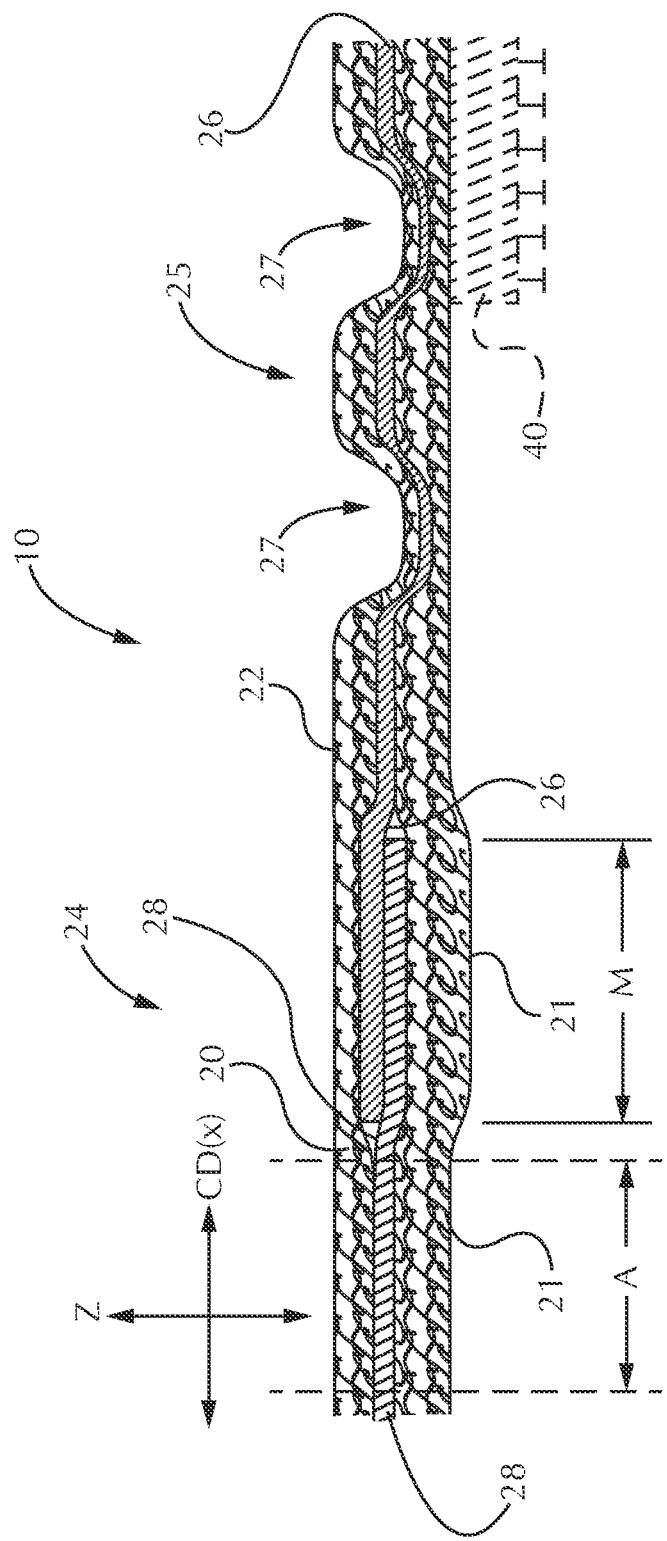
FIG. 3 is a schematic, cross-sectional view of a portion of a material web.

As suggested by FIG. 3, elastomeric film layer 28 may be situated so as to lie substantially within the first region 24 but not in, or in only a portion of, second region 25. This may be desired in applications in which it is desired that members cut from web 10 have elastic extensibility in portions cut from first region 24, but in which elastic extensibility is not needed or is undesirable in portions cut from second region 25, such as a tab portion having a fastener affixed thereto. However, as suggested by FIG. 3, elastomeric film layer 28 also may be situated so as to lie partially in second region 25, thereby overlapping a portion of polymeric film layer 26 by overlap margin M, so as to impart tensile strength and tear resistance to the web in the cross direction, at the junction between the elastomeric film layer and second region 25. For fastening members of the type contemplated herein, an overlap margin M from 2 mm to 10 mm wide may be desired to strike a balance between the benefits of added tensile strength, and unnecessary overusage of materials.

Referring to FIGS. 1, 3 and 4, first region(s) 24 or portions thereof may be activated or incrementally stretched in extensible zone A according to the process described in, for example, U.S. Pat. Nos. 5,167,897; 5,156,793; and 5,143,679; or U.S. application Ser. No. 10/288,095; 10/288,126; 10/429,433; 11/410,170; 11/788/231; 11/811,130; 11/899,656; 11/899,810; 11/899/811; 11/899,812; 12/204,844; 12/204,849; 12/204,854; 12/204,858; or 12/204,864, the disclosures of which are incorporated herein by reference, to make the laminate elastically extensible. As an alternative to use of the above-referenced methods, an elastically extensible stretch laminate may be formed by laminating an elastic film layer 28 in a pre-strained condition (e.g., at least in extensible zone A) to one or more layers of nonwoven in a substantially unstrained condition. When the resulting laminate is allowed to relax by contraction of the elastic, the nonwoven layer(s) form gathers or rugosities of gathered material transverse to the direction of pre-strain of the elastic member, which are then available to permit and accommodate stretching of the laminate along the direction of pre-strains of the elastic member. In extensible zone A, the laminate may be activated or incrementally stretched in the cross (x) direction, or manufactured by laminating elastic film 28 with the nonwoven layer(s) while elastic film 28 is pre-stretched condition along the cross (x) direction.

Activation or incremental stretching may have the effect of providing roughly linear zones of separation, elongation and/or breaks in fibers of first nonwoven layer 20 and second nonwoven layer 21 (if present), substantially perpendicular to the stretch direction. Such separation, elongation and/or breaks in the fibers provide extensibility of the laminate web in the direction of stretch, that would otherwise be kept limited by or would be undesirably destructive of, fibers of first nonwoven layer 20 and second nonwoven layer 21 (if present) oriented along the direction of stretch. In addition, in a laminate to be activated to impart extensibility in the cross direction, first nonwoven layer 20 and/or second nonwoven layer 21 (if included) may be selected such that the fibers thereof have a machine direction orientation. This may complement the activation process and its effects, by reducing the numbers of fibers that are separated or broken during activation and thereby reducing the number of loose or hanging, broken fibers that may result from the cross-direction stretching effected by the activation rollers.

An example of a use for web 10 as described above can be appreciated from FIGS. 4 and 5. Web 10 may be passed in a machine direction MD through a cutting mechanism, such as a pair of rollers comprising an anvil roller and an opposing cutting die-bearing roller (not shown), which cut the web along cutout profiles 31. In this manner, members such as a fastening member 30 (FIG. 5) may be produced. Fastening member 30 may have a proximal end 32, a distal end 33, a first lateral edge 34 and a second lateral edge 35. Fastening member 30 may also have a fastener component, such as a patch of hooks 40 (hooks component of a hook and loop fastening system) affixed to, for example, distal portion 36 cut from second region 25, in a previous or subsequent step. First region 24 may include an elastomeric film layer and an extensible zone A, as described above. Such a fastening member 30 may be attached along its proximal end 32 to a wearable article, for example, a disposable diaper, at a waist portion thereof. Examples of fastening members of this type are depicted in U.S. application Ser. No. 12/904,220, the disclosure of which is incorporated herein by reference. In another example, fastening members may be designed to have partially or entirely complementary, nested shapes, such that cutout paths 31 are partially or entirely merged and one cutout path traces outlines of two adjacent fastening members, simplifying the design of the required cutting die-bearing roller and reducing or eliminating cutaway waste.

Figure 14:
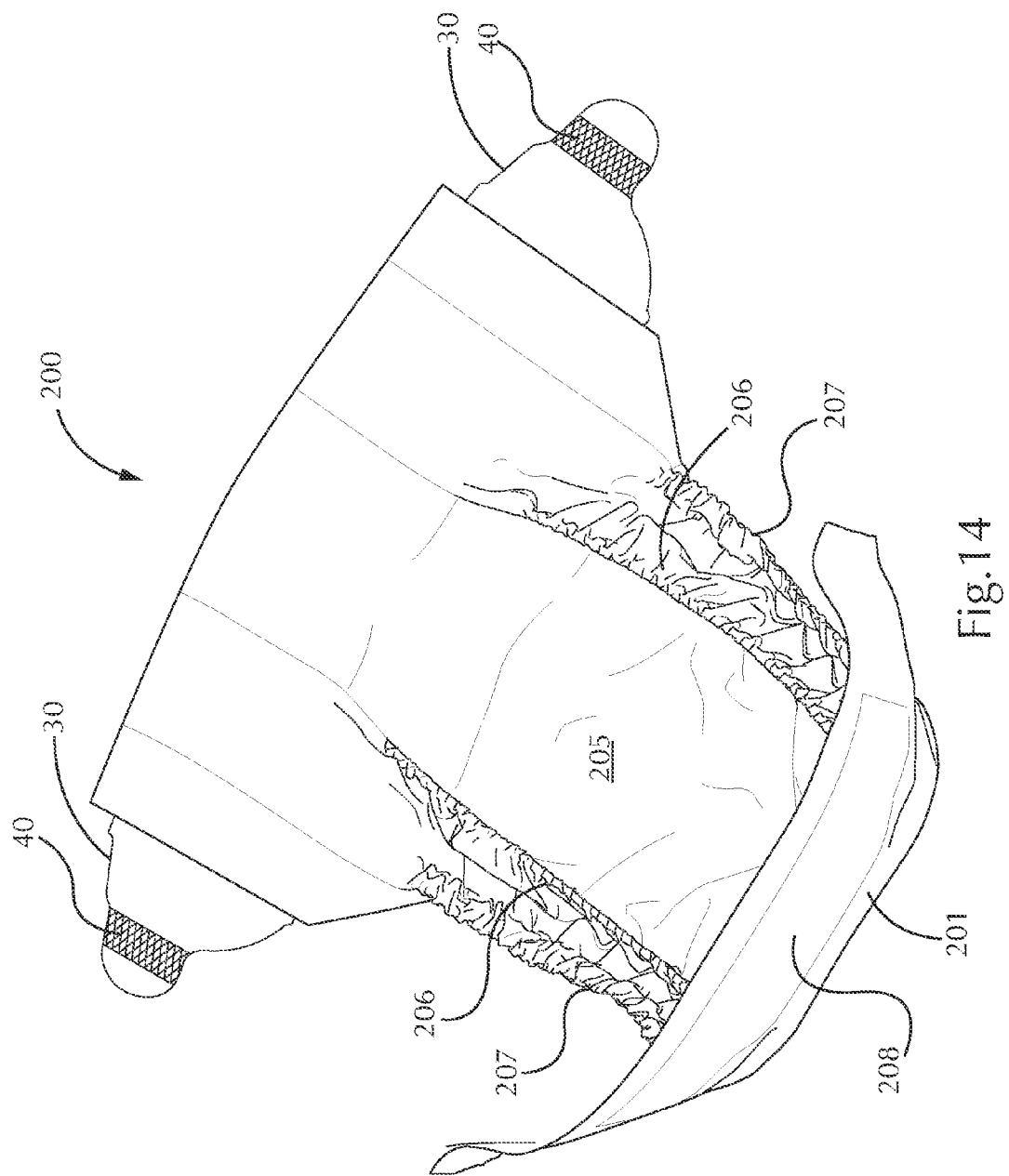
FIG. 14 is a perspective view of an absorbent article in the form of a diaper, shown generally in a relaxed condition with wearer-facing surface upward, with contraction and foreshortening induced by the presence of elastic members in barrier cuffs and leg cuffs.
Figure 15:
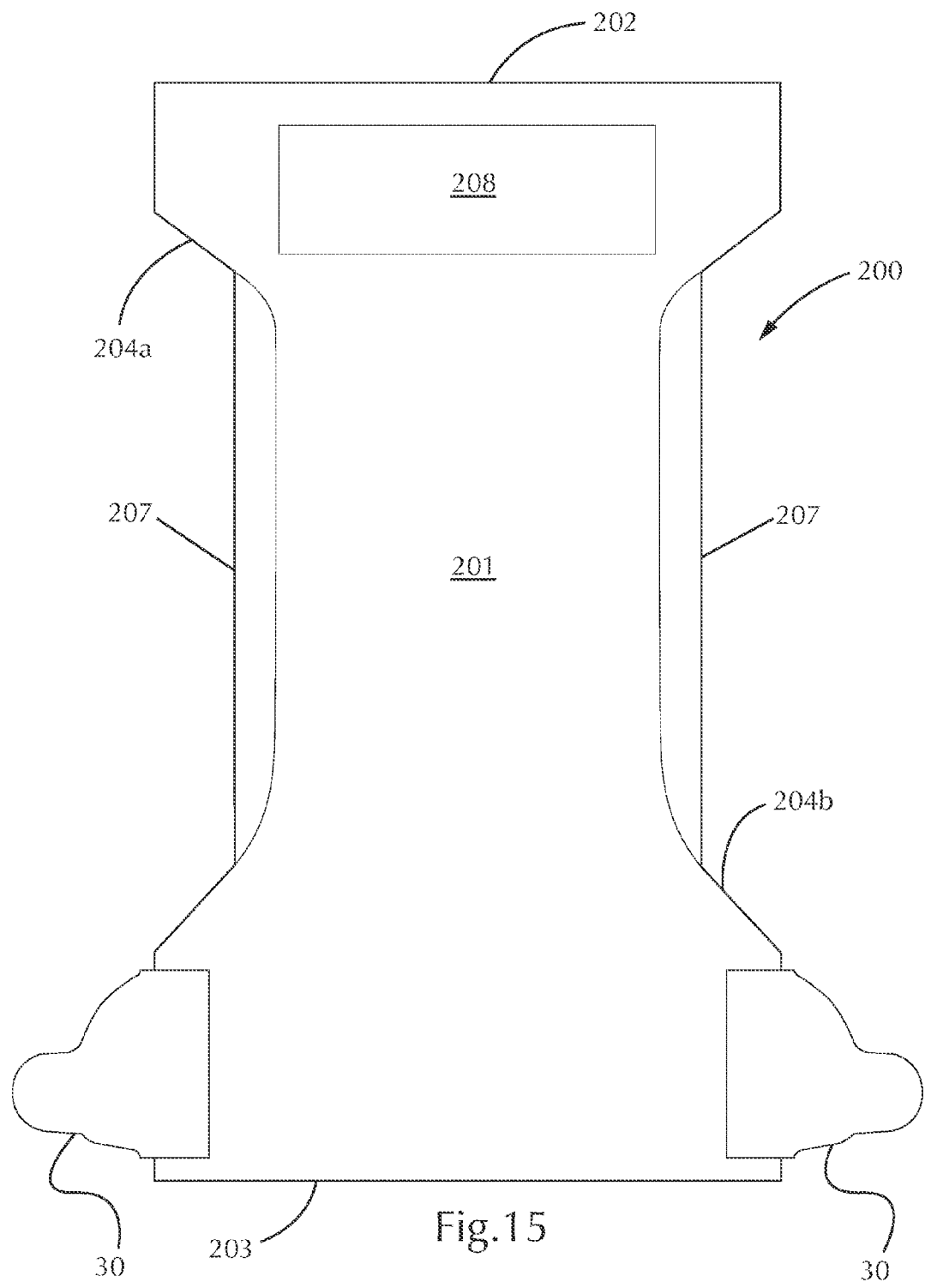
FIG. 15 is a plan view of an absorbent article in the form of a diaper, shown generally in a stretched condition with the outward-facing surface facing the viewer, whereby contraction and foreshortening induced by the presence of elastic members are removed.

A fastening member such as fastening member 30 may be attached to an article such as diaper 200 to provide a mechanism for fastening the diaper about a wearer, as suggested in FIGS. 14 and 15. Diaper 200 may include a outward-facing liquid impermeable backsheet 201 having lateral front 202 and rear 203 waist edges and a pair of longitudinal edges 204a, 204b joining them, a wearer-facing liquid permeable topsheet 205, an absorbent core (not specifically shown) disposed between the topsheet and backsheet, a pair of longitudinal barrier cuffs 206, and a pair of leg bands 207; the barrier cuffs and/or leg bands may be elasticized. As suggested in FIGS. 14 and 15, a pair of fastening members 30 may be attached to the backsheet 201 on the outward-facing surface thereof, or on the inner-facing surface. Diaper 200 also may include a landing zone 208, which may be a patch of loop material adapted to serve as one component of a hook-and-loop fastening system, where each fastening member 30 includes a patch of hooks 40 as described above. Landing zone 208 may be formed of a patch of loop material adhered to the backsheet, a patch of nonwoven material adapted for use as a loops component, or even simply the nonwoven outer layer of the backsheet, if sufficiently robust to provide secure fastening by a patch of hooks. Landing zone 208 may be visibly defined or delineated by printing on the backsheet or on the landing zone material, or other means, to inform a caregiver where to attach fastening members 30.

It will be appreciated from the description above that a fastening member 30 so formed may be imparted with several advantageous features and benefits. If an elastomeric film layer 28 (see FIG. 3) is included and the web is activated or formed with pre-strained elastomeric film as described above, fastening member 30 may be imparted with elastic extensibility in the cross direction, in extensible zone A. If a fastening member is cut from web 10 in a manner suggested in FIG. 4, a portion of second region 25 of web 10 forms the distal portion 36 of fastening member 30 (as suggested in FIG. 5). Thus, distal portion 36 will be a reinforced portion of the fastening member, through inclusion of the polymeric film layer 26 in second region 25, from which the fastening member may be cut. Reinforced distal portion 36 may thus be better adapted to sustain and disperse stresses that may tend to result and undesirably concentrate from a reducing width or tapering geometry of the fastening member and/or inclusion of an affixed fastener component on distal portion 36 and tension in the fastening member resulting from tugging and pulling that may occur during, for example, application and wearing of a wearable article of which fastening member 30 may be made a part.

The designer of a wearable article (such as a diaper) bearing a fastening member such as fastening member 30 may determine that users of the article are likely to subject the fastening member to concentrations of stresses that are greater along one of lateral edges 34, 35 than along the other. In this event, tearing under excessive stresses may be more likely to propagate in use from the side edge along which stresses are more concentrated, and propagate generally along a particular direction. Thus, for example, stresses in fastening member 30 during application and use may in some circumstances be concentrated more along side edge 35 than along side edge 34, making a tear beginning at side edge 35 more likely. As a result of the orientation in which the fastening member 30 may be situated relative the article to which it is attached, and the manner in which caregivers often grasp and tug such fastening members, tears may be more likely to propagate in the machine direction of the fastening member (30).

Without intending to be bound by theory, it is believed that the materials within bond sites 27 may be more brittle and/or more likely to tear under stress, as a result of their consolidation under pressure, and in some circumstances, thermal energy, during the bonding process. At the same time, materials forming layers 20, 26 and, where included, 21 (see FIG. 2) together may be more resistant to tearing and form a quite tear-resistant composite where not bonded together, since they have not been deformed by bonding. For these reasons, the designer may elect to impart bond sites 27 with particular features, particularly bond sites that will be proximate to relatively high-stress areas in their end-use.

Figure 6:
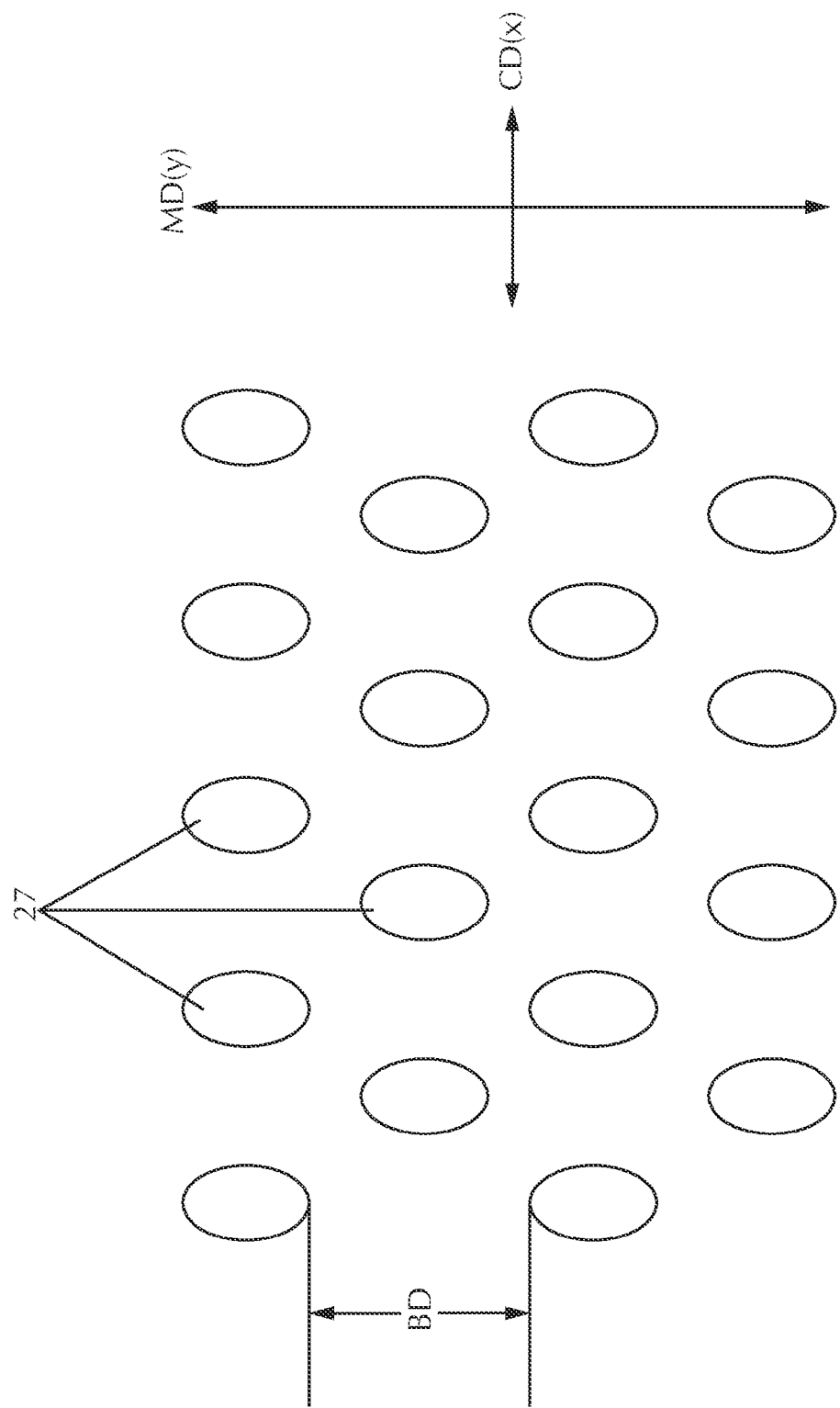
FIG. 6 is a schematic, plan view of a bonding pattern.

Referring to FIG. 6, bond impressions at bond sites 27 may have rounded shapes. FIG. 6 depicts bond impressions with oval shapes. Bond impressions may also have circular shapes, oval shapes, ovaloid shapes, elliptical shapes, egg-shapes, "race-track"-shapes, or any other shapes that have generally rounded profiles without macroscopically observable sharp corners. Other examples of tear propagation-resistant bond impression shapes and patterns may be seen in U.S. Pat. Nos. 6,620,490; 6,713,159; 6,717,028; and 6,837,961, the disclosures of which are incorporated herein by reference. Without intending to be bound by theory, it is believed that, because such shapes are bounded by profiles in the adjacent unbounded materials that have no sharp corners, concentrations of stresses that may occur in sharp inside corners of materials are avoided, and thus, tear propagation through the web material is less likely.

It can also be appreciated from the example of FIG. 6 that the distance BD between the bond sites may greatest along the machine direction MD. This greatest distance represents the greatest path a tear must propagate through unbounded materials in order to propagate between adjacent bond sites 27. As noted above, the materials forming the layers of the web material may be most resistant to tearing in their unbonded regions. Thus, a designer may want to arrange bond sites such that the greatest distance between adjacent bond sites in a pattern occurs along a direction perpendicular to stresses to be imposed upon the web material when in its end use. Thus, for example, when the finished product to be cut from the web will undergo its greatest stresses during end use in the cross direction CD, these may tend to propagate tears in the machine direction MD, and the designer may want to arrange bond sites such that the greatest distance between bond sites lies along the machine direction MD—as suggested in FIG. 6.

As noted above, it is believed that material within bond sites 27 will tear more readily than adjacent, unbonded materials forming the web. Accordingly, another approach a designer may wish to employ is to minimize the bonding area used to bond the respective layers, thus minimizing the area of material more subject to tearing and maximizing the area of unbonded layers more resistant to tearing. At the same time, a minimum amount of patterned bond area is necessary to form a unitary multilayer web. Accordingly, it may be desired that the bond area (i.e., area occupied by bond impressions at bond sites 27) be in the range of 1 to 20 percent, where the percentage is the ratio of area occupied by the bond impressions to the total surface area of the web in the region which includes the polymeric film layer 26.

Figure 9:
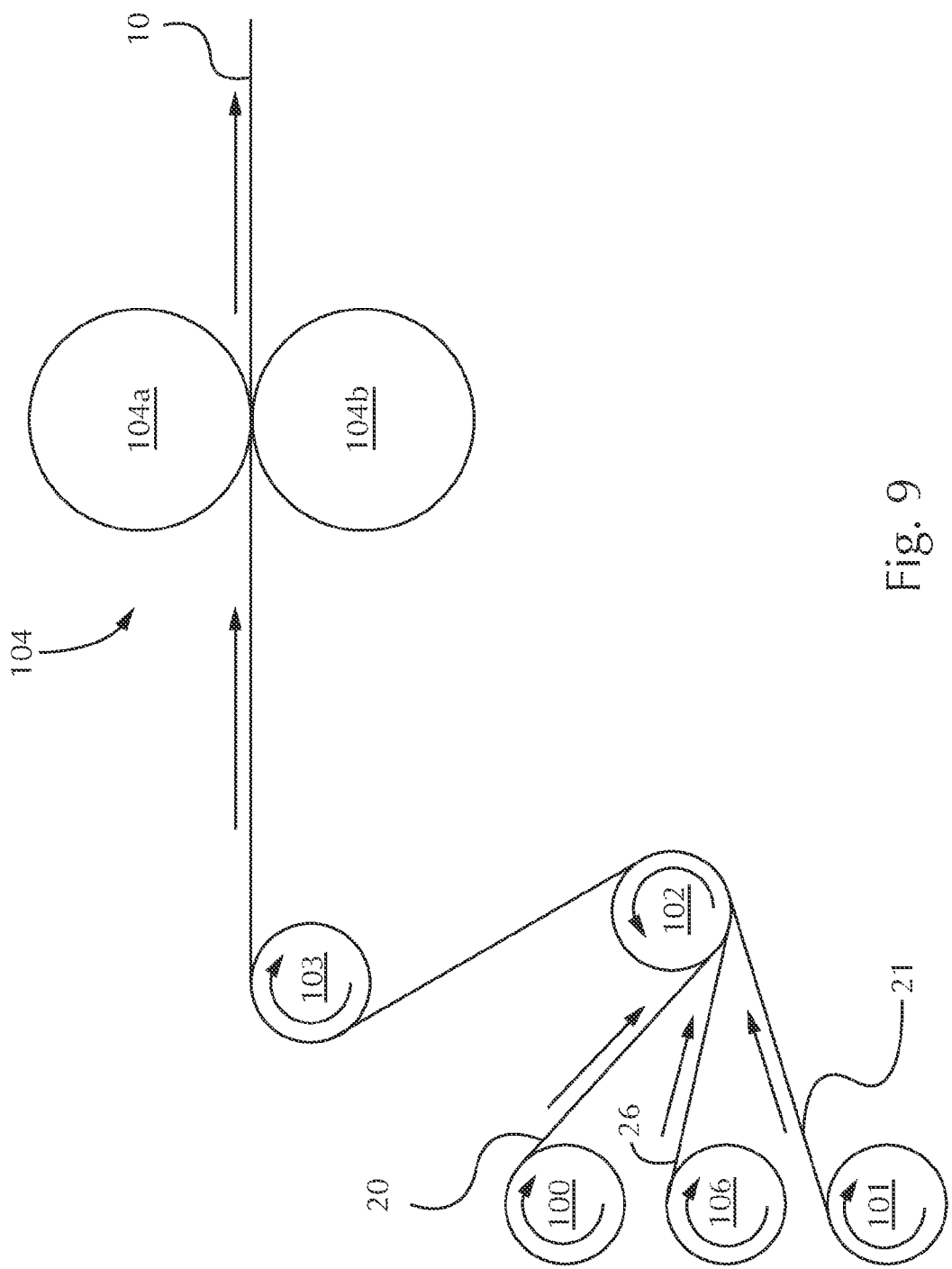
FIG. 9 is a schematic depiction of a process for manufacturing a web with a bonded reinforcing layer.

An example of a process for producing components of web 10 as depicted in FIGS. 1-3 is depicted schematically and in side view/partial cross section in FIG. 9. In the example, nonwoven layer 20, polymeric film 26, and nonwoven layer 21, are drawn from supplies such as, respectively, supply rolls 100, 106, 101, and brought together and moved in a machine direction in superimposed relationship over one or more consolidating and/or tensioning rollers 102, 103, and then drawn into the nip between a pair of bonding rollers 104a, 104b. Bonding rollers 104a, 104b or circumferential surfaces thereof may be formed of steel.

One or both of bonding rollers 104a, 104b may have a circumferential surface having thereon a pattern of raised protuberances and/or depressions corresponding to the shape and pattern of bond sites desired, while one of bonding rollers 104a, 104b may have a relatively smooth circumferential surface without any protuberances or depressions. Alternatively, a first circumferential surface of a first of bonding rollers 104a, 104b may have a pattern of raised features corresponding to the shape and pattern of bond impressions desired, while a second circumferential surface of the second of the bonding rollers 104a, 104b may have correspondingly shaped and patterned depressions, thereby constituting a "negative" or mating surface that meshes with the first surface when the bonding rollers are brought together with their axes parallel. At least one of bonding rollers 104a, 104b, may be heated so as to transfer heat, by contact with the materials as they pass through the nip, and may thereby promote thermal fusing or welding of layers at bond sites.

In another example, the bonding rollers 104a, 104b may be run without adding heating energy, but under sufficient forces urging them together at the nip, such that rapid material compression and deformation occurs beneath the protuberances as the component layers move through the nip. Such rapid material compression and deformation brought about by sufficient nipping force coupled with sufficient web speed can effect material bonding at or about the protuberances as a result of friction within the deforming materials causing heating, and material fusion, mechanical intertangling/intermeshing of materials, or a combination of both effects. Bonding rollers 104a, 104b may be mounted and disposed in connection with a structure and mechanism (not shown) that urges them together at the nip at a desired, controllable force. The force applying mechanism may be used to regulate the amount of force exerted by the protuberances that compress the materials in the nip. The force applying mechanism may be, for example, a mechanism including one or more hydraulic and/or pneumatic cylinders, wherein fluid pressure may be applied and controlled to effect exertion of the desired force. Examples of suitable bonding mechanisms utilizing rollers are described in, for example, U.S. Pat. Nos. 4,854,984 and 4,919,738, issued to Ball et al.

In still another example, one of the rollers 104a, 104b may have bonding protuberances as described above, while the other may be a rotating sonotrode, or alternatively, not a roller at all, but rather, a fixed sonotrode having a smooth surface facing the protuberance-bearing roller. The sonotrode may be used to transmit ultrasonic energy to the material concentrated at the protuberances, effecting rapid heating and promoting thermal bonding or fusing beneath the protuberances. A rotating sonotrode may be desired because it may avoid clogging or fouling at the nip, by fibers, or by deposits of melted polymer components of the layers passing through the nip.

One or both of bonding rollers 104a, 104b may be driven by motor(s) such that the linear speed of their circumferential surfaces corresponds with the desired web processing speed. Thus, the bonding rollers 104*a*, 104*b* may be the mechanism by which layers 20, 26, 21 are drawn from their respective supplies.

As the superimposed layers enter and pass through the nip, the combination of pressure applied by and/or heating energy concentrated at, the protuberances, compresses the layers together and heats them beneath the protuberances. As a result, the materials of the layers may at least partially melt and fuse together beneath the protuberances, resulting in creation of bond sites 27 in the web, having shapes and patterns corresponding with the shapes and patterns of the protuberances on the bonding roller(s).

Referring to FIGS. 1, 2 and 9, the supply 106 of polymeric film layer 26 may have a cross-direction width that is less than the cross-direction width of one or both of nonwoven layers 20, 21. Accordingly, bonding rollers 104*a*, 104*b* may have a correspondingly narrower width, or alternatively, the pattern of raised features along the circumferential surface thereof may be narrower, so as only to effect compression and, where employed, input of thermal energy or heating along the portion of the laminate including the polymeric film layer, and not along the entire widths of the nonwovens. Referring to FIG. 1, a narrower polymeric film layer may be disposed at any location along the cross-direction width of the nonwoven layer(s). Additionally, it will be appreciated that more than one strip of polymeric film layer may be disposed along the cross-direction widths of the nonwoven(s) to create a web with a plurality of reinforced zones along its width. Bonding roller pairs may be configured and spaced in the cross direction accordingly. Additional steps of supplying an additional elastomeric member(s) or elastomeric film layer, applying adhesive as may be required and completing lamination of layers 20, 26, 28 (if included) and 21 (if included), may be performed upstream or downstream, or concurrently in the above-described bonding process.

Figure 7:
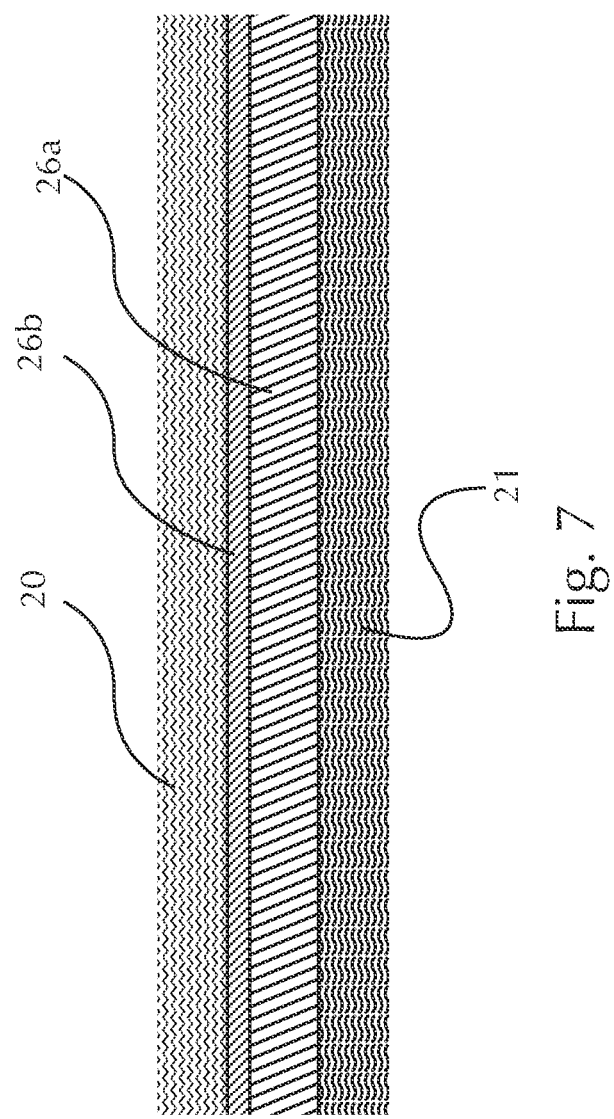
FIG. 7 is a schematic cross-sectional view of a portion of a material web.
Figure 8:
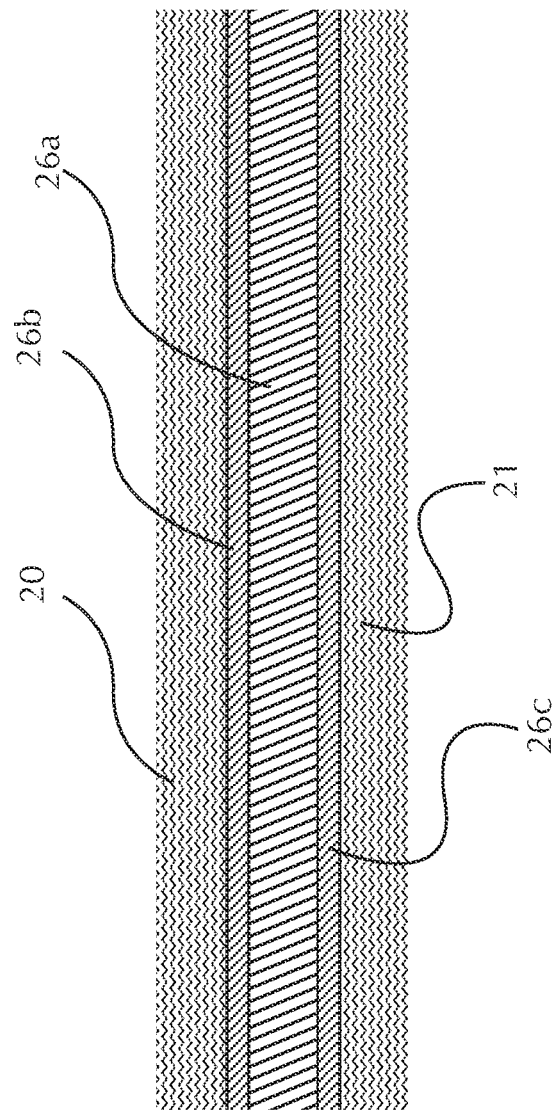
FIG. 8 is a schematic cross-sectional view of a portion of a material web.

Referring to FIGS. 7 and 8, polymeric film layer 26 also may comprise one or more polymers such as a polyethylene, a polypropylene, or combinations thereof, as mixtures or as layered film components. A plurality of discrete film layer components may be coextruded to form film layer 26. In one example, a base layer 26*a* may be formed of a polymer selected for a first combination of cost and/or mechanical attributes and physical properties. In one particular example, base layer 26*a* may be formed of polypropylene, particularly a polypropylene homopolymer, which may be deemed suitable for uses of the type described herein as a result of its relative cost, mechanical attributes and physical properties. In other examples, base layer 26*a* may be formed of cyclo-olefin copolymers, styrene polymers, polyamides, polylactides, thermoplastic polyurethanes, or blends of the foregoing.

A first skin layer 26*b*, and, if desired, second skin layer 26*c*, may be included, formed of polymers selected for combination(s) of cost and/or mechanical attributes and physical properties differing from those of the base layer 26*a*. In one example, first and second skin layers 26*b* and 26*c* may be formed of polyethylene or a blend including a predominant (by weight) polyethylene constituent, for reasons that will become apparent in the description below.

The bonds formed at the bond sites 27 may consist of a mechanical intertangling or intermeshing of respective structures and materials of the first nonwoven layer, or even thermal fusing and/or welding between the polymeric film layer 26 and first 20 and second 21 (if present) nonwoven layers, caused by compression, deformation and/or heating of the structures beneath the protuberances at the nip between the bonding rollers. Polymeric materials of like chemistry may make good bonding couples because of the chemical and mechanical behavior compatibility of the species present under the bonding protuberances. Thus, if polymeric materials of like chemistry are urged together in the nip, bonds formed between them may be relatively more strong and stable. For example, if the nonwoven layer(s) 20, 21 comprise in part or in whole polypropylene fibers and the polymeric film layer comprises a like polypropylene, melting and compression may cause the polypropylene of the nonwoven layer fibers and that of the polymeric film layer to form bonds between molecule chains, thereby effectively creating fused or welded regions in and about the periphery of the bond sites. Thus, it may be desirable in some circumstances for components in the nonwoven layer(s) and component(s) in the polymeric film layer to be of one or more like polymer(s).

Still referring to FIGS. 7 and 8, it may be desired that one or both nonwoven layers 20 and 21 (if included) be formed of separate constituent fibers formed of a first polymer and a second polymer, such as polyethylene fibers blended with polypropylene fibers. Alternatively, the nonwovens may be formed homogeneously of fibers, the fibers formed of single-polymer or multi-polymer component resins, such as blended polyethylene and polypropylene resins. As an alternative, one or both of the nonwoven layers may be formed of fibers having cross sections of discretely identifiable polymer sections, known as bicomponent or multicomponent fibers, which have a first component section of a first polymer such as a polypropylene, and a second component section of a second polymer such as a polyethylene.

Polypropylene has relatively greater stiffness and tensile strength, which properties make it generally desirable as a component of constituent fibers for nonwovens of the types contemplated herein, for purposes of strength of the nonwoven. However, polypropylene also is relatively less ductile; thus, constituent fibers formed of polypropylene, in a nonwoven, may tend to break excessively when the nonwoven is subjected to an activation or incremental stretching process. This may result in the nonwoven partially disintegrating and/or becoming partially detached from a laminate, as a result of activation.

Polyethylene is relatively more elastic and ductile than polypropylene, and fibers formed of it may improve toughness and elongation capability of a nonwoven, and impart better friction and wear behavior. Polyethylene fiber components may improve the ability of a nonwoven to retain its integrity through an activation process. Additionally, fibers formed of polyethylene typically have more pleasing tactile attributes including a more smooth/slippery feeling surface, and more pliability.

Forming nonwovens of fibers of two or more polymers may enable enjoyment of the advantages provided by each. Bicomponent or multicomponent fibers may be used to form a nonwoven. In one example of a bicomponent nonwoven constituent fiber, the fiber may have a core of a first polymer and a sheath or cladding of a second polymer. For example, the fiber may have a core section of polypropylene and a sheath or cladding section of polyethylene. In another example of a bicomponent nonwoven constituent fiber, the fiber may have first and second sections arranged in a side-by-side or other cross-sectional configuration. The first section may be polypropylene and the second section may be polyethylene.

Referring again to FIGS. 7 and 8, if the nonwoven layer(s) 20, 21 have components of a particular polymer, then the film layer 26 may be provided with a base layer 26*a* and one or two skin layer(s) 26*b*, 26*c*, the skin layer(s) formed of a polymer of like chemistry to enhance bonding as explained above. In one example, nonwoven layer(s) 20 and/or 21 may include polyethylene components, and film 26 may have a base layer 26*a* and one or two skin layer(s) 26*a*, 26*b* which also are formed of polyethylene, that face the nonwoven layer(s) 20, 21 having polyethylene components. The base layer 26*a* may be formed of a polymer such as a polypropylene.

A polypropylene may be desired for inclusion in one or both the base layer of film layer 26 and in the fibers of a facing nonwoven layer, e.g., layers 20, 21, for its mechanical properties such as relative stiffness, tensile strength and relatively higher melting temperature. It may be desired that the base layer 26*a* be a polypropylene homopolymer. Other components that may be suitable include cyclo-olefin copolymers, styrene polymers, polyamides, polylactides, thermoplastic polyurethanes, PET, or blends of any of these.

A polyethylene component may be desired in a skin layer because, among other properties noted above, it will be of like chemistry with polyethylene components of nonwoven fibers. Additionally, polyethylene may have a relatively lower melting temperature. For this reason, it may provide a way to create a thermally-fused bond with polyethylene fiber components without the necessity of melting the other components, such as polypropylene components—which requires greater energy input, and may unacceptably compromise their structural integrity. Thus, it may be desired that the skin layer of the film layer 26 be formed of a polyethylene. Low-density polyethylene (LD-PE), linear low-density polyethylene (LLD-PE), or very low-density polyethylene (VLD-PE) may be suitable for the skin layer of film layer 26. These polymers may also be suitable for the sheath, cladding or other component section of a bicomponent or multicomponent fiber constituent of a nonwoven layer.

For a laminate to be used to form fastening members for diapers, and in a film layer 26 thereof having a skin layer of polyethylene and base layer of polypropylene, it may be desired that the base layer have sufficient thickness in order to achieve the desired stiffness and tensile properties, but not more—for cost control reasons. It may be desired that the base layer have a thickness between 20 μm and 100 μm. It may be desired that the skin layer(s) 26*b*, 26*c* have sufficient thickness to provide sufficient material for effecting suitably strong thermal bonds with the nonwoven, but not more—again, for cost control reasons. Thus, it may be desired that the skin layer have a thickness between 2 μm and 20 μm.

Referring to FIG. 7, in one example, a laminate may be formed from a film layer 26 having a skin layer 26*b* formed of a polyethylene and a base layer 26*a* formed of a polypropylene. A first nonwoven layer 20 having constituent bicomponent fibers, having a polyethylene section component and a polypropylene section component, may face the skin layer 26*b*. A second nonwoven layer having constituent monocomponent polypropylene fibers may face the polypropylene base layer. In this configuration, the bond strength between the skin layer and the bicomponent fiber nonwoven layer may be greater than the bond strength between the base layer and the monocomponent nonwoven layer, as a result of the differing melt temperatures of the polyethylene and polypropylene components. This may have a positive effect on the tear resistance of the laminate.

In another example, a nonwoven rather than a film may be used to form layer 26, this nonwoven may include or be formed of single-component, bicomponent or multicomponent fibers having a component of like chemistry with a component of the fibers of first nonwoven layer 20. The fibers of a nonwoven layer 26 may have polyethylene outer sheaths or sections forming a portion of their outer surfaces. This may provide bond strength between layer 26 and layers 20 and/or 21 by creating a thermally-fused bond with the polyethylene fiber components of the first and/or second side of the nonwoven layers 20 and/or 21 without the necessity of melting the other components, such as polypropylene components—which requires greater energy input, and may unacceptably compromise their structural integrity. A laminate having both first and second layers 20 and 26 formed of nonwovens with respective fiber components of like chemistry may be combined with any of the other features (third and fourth layers, bonding patterns and shapes, etc.) described herein as an alternative to use of a film for second layer 26.

It is believed that the process and materials described herein provide a way in which to provide reinforcing for a nonwoven web with a relatively cost-effective selection and application of materials. From the foregoing it will be appreciated that the construction of a fastening member as described may serve to eliminate the need for attachment of a discrete fastening tape bearing a fastening component, to the distal portion of a stretchable fastening member, as is currently in widespread practice. The described web and fastening member construction provides for a fastening member with a neat, continuous, integrated appearance, allows for manufacturing efficiency and savings, and provides structural advantages over fastening members of current designs.

Stiffness Test

Figure 10:
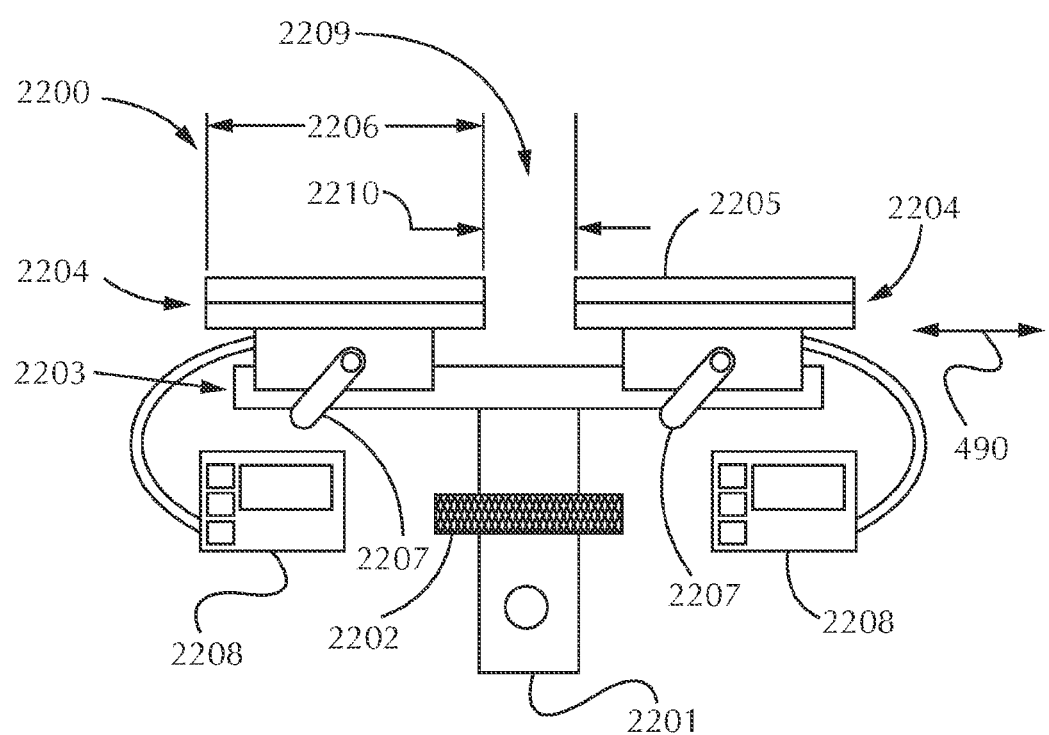
FIG. 10 is an elevation view showing an apparatus for testing the bending stiffness of materials.
Figure 11:
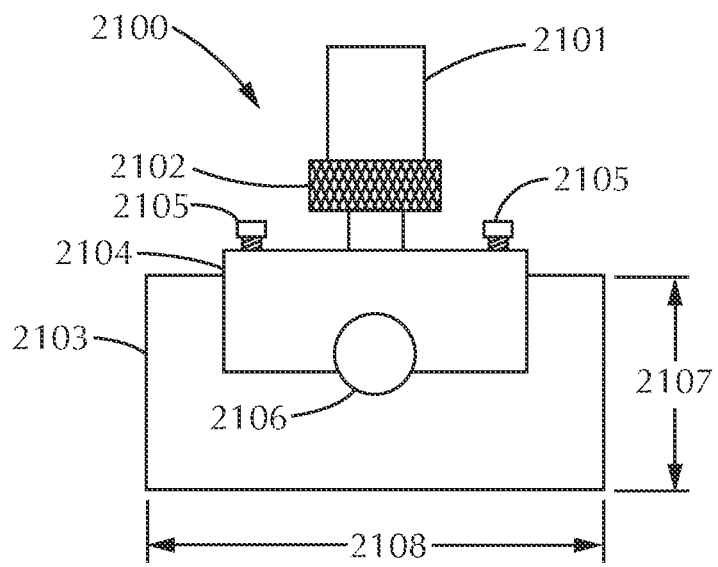
FIG. 11 is a front elevation view showing a plunger for use with the apparatus of FIG. 10.
Figure 12:
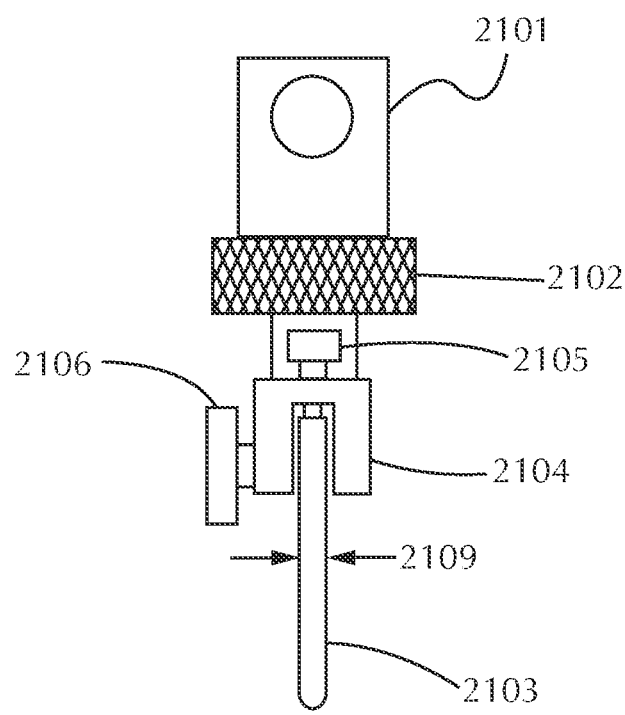
FIG. 12 is a side elevation view showing a plunger for use with the apparatus of FIG. 10.

Stiffness is measured using a constant rate of extension tensile tester with computer interface (a suitable instrument is an MTS Alliance under TestWorks 4 software, as available from MTS Systems Corp., Eden Prairie, Minn.) fitted with a 10 N load cell. A plunger blade 2100, shown in FIG. 11 (front view) and FIG. 12 (side view), is used for the upper movable test fixture. Base support platforms 2200, shown in FIG. 10, are used as the lower stationary test fixture. All testing is performed in a conditioned room maintained at about 23 C±2 C and about 50%±2% relative humidity. Herein, width and length of the test specimen are a lateral width and longitudinal length using the directional conventions corresponding to the fastening member from which the specimen is cut, as "lateral width" and "longitudinal length" are defined herein.

Components of the plunger 2100 are made of a light weight material such as aluminum to maximize the available load cell capacity. The shaft 2101 is machined to fit the tensile tester and has a locking collar 2102 to stabilize the plunger and maintain alignment orthogonal to base support platforms 2204. The blade 2103, has a length 2108 of 115 mm, a height 2107 of 65 mm, and a thickness 2109 of 3.25 mm, and has a material contact edge with a continuous radius of 1.625 mm. The bracket 2104 is fitted with set screws 2105 that are used to level the blade and a main set screw 2106 to firmly hold it in place after adjustment.

The bottom fixture 2200 is attached to the tensile tester with the shaft 2201 and locking collar 2202. Two movable support platforms 2204 are mounted on a rail 2203. Each test surface 2205 has a width 2206 of 85 mm and a length of 115 mm (into plane of drawing) and is made of polished stainless steel so as to have a minimal coefficient of friction. Each platform 2204 has a digital position monitor 2208 which reads the individual platform positions, and set screws 2207 to lock their position after adjustment. The two platforms 2204 are square at the gap edge and the plate edges should be parallel front to back. The two platforms form a gap 2209 with an adjustable gap width 2210.

Accurately (±0.02 mm) align the plunger blade 2103 so that it is orthogonal to the top surfaces 2205 of the support platforms 2204 and exhibits no skew relative to their edges defining the gap 2209. Using the position monitors 2208, accurately set the gap width 2210 to 8.00±0.02 mm between the two edges of the support platforms 2204 defining the gap 2209, with the thickness 2109 of plunger blade 2103 accurately (±0.02 mm) centered in the gap 2209, and length 2108 of plunger blade 2103 parallel the edges of platforms 2204 defining the gap 2209. Program the tensile tester for a compression test. Set the gauge length from the bottom of the plunger blade 2103 to the top surface of the support platform 2204 to 15 mm.

Set the crosshead to lower at 500 m/min for a distance of 25 mm. Set the data acquisition rate to 200 Hz.

Precondition specimens at about 23 C±2 C and about 50%±2% relative humidity for 2 hours prior to testing. Die cut test specimens 13 mm in width by 25.4 mm in length. If the fastening member from which the test specimens are to be cut does not have sufficient material for test specimens of these dimensions, use the full dimensions that are available for a comparison of stiffness of specimens cut from the distal region and proximal region, of equal sizes.

Examine the specimens for any exposed adhesive and deactivate any exposed adhesive by applying baby powder to it as necessary. Place the specimen flat onto the surface of the support platform 2204 over the gap 2209 with the fastener side facing upward. Center the specimen across the gap; the specimen length dimension should be parallel to the gap width 2210 dimension and the specimen width dimension should be perpendicular to the gap width 2210 dimension. Zero the load cell; start the tensile tester and the data acquisition.

Figure 13:
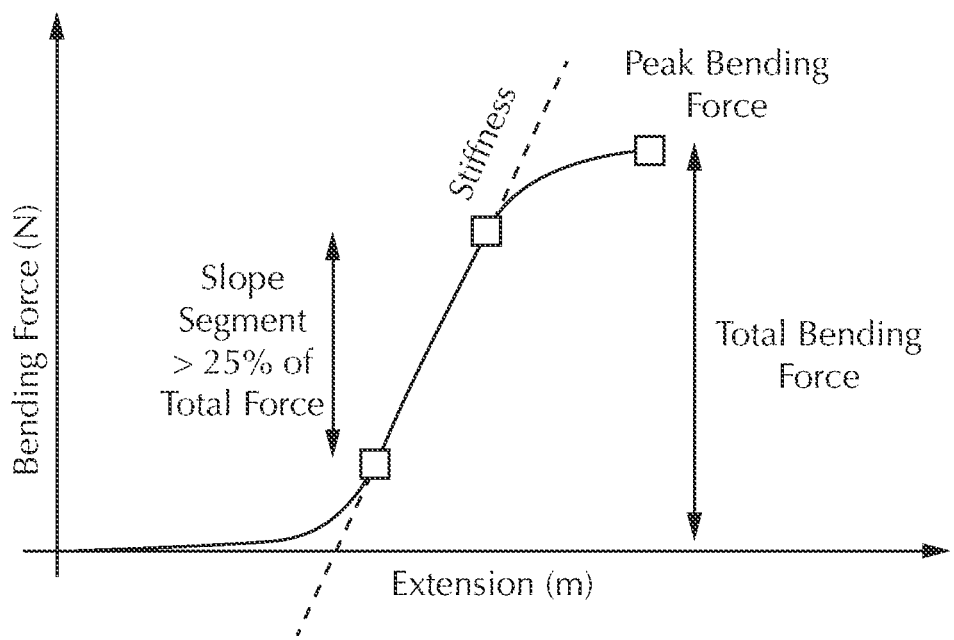
FIG. 13 is a graph showing Peak bending load and slope calculation areas on bending curve.

Program the software to calculate the maximum peak bending force (N) and Stiffness (N/m) from the constructed force (N) verses extension (m) curve. Stiffness is calculated as the slope of the bending force/extension curve for the linear region of the curve (see FIG. 13), using a minimum line segment of at least 25% of the total peak bending force to calculate the slope. If the width of the element is not 13 mm, normalize the actual width to 13 mm as follows:

Stiffness$_{(actual\ width)}$=[Stiffness$_{(13\ mm)}$/13 mm]×actual width (mm)

peak bending force$_{(actual\ width)}$=[peak bending force$_{(13\ mm)}$/13 mm]×actual width (mm)

Report peak bending force to the nearest 0.1 N and the Stiffness to the Nearest 0.1 N/m.

Hysteresis Test

The following test methods utilize a commercial tensile tester (e.g., from Instron Engineering Corp. (Canton, Mass.), SINTECH-MTS Systems Corporation (Eden Prairie, Minn.) or equivalent) interfaced with a computer. The computer is used to control the test speed and other test parameters and for collecting, calculating, and reporting the data. The tests are performed under laboratory conditions of 23° C.±2° C. and relative humidity of 50%±2%. The samples are conditioned for 24 hours prior to testing.

1. Select a 2.54 cm (width), 7.62 cm (length) sample of the material for testing. In some cases, if it is not be possible to get a 2.54 cm×7.62 cm sample, a smaller sample may be used, but a gage length of 25 mm must still be used. If the sample is activated or includes an activation portion, the length of the sample is taken in the direction of activation.

2. Select the appropriate jaws and load cell. The jaws must have flat surfaces and must be wide enough to fit the sample (e.g., at least 2.54 cm wide). Also, the jaws should provide adequate force to ensure that the sample does not slip during testing. The load cell is selected so that the tensile response from the sample tested is between 25% and 75% of the capacity of the load cell used.

3. Calibrate the tester according to the manufacturer's instructions.

4. Set the distance between the grips at 25 mm.

5. Place the sample in the flat surface of the jaws such that the longitudinal axis of the sample is substantially parallel to the gauge length direction. Mount the sample with minimal slack. Set the slack preload at 0.02 N/cm. This means that the data collection starts when the slack is removed with a force of 0.02 N/cm. Strain is calculated based on the adjusted gauge length ($l_{ini}$), which is the length of the sample in between the grips of the tensile tester at a force of 0.02 N/cm. This adjusted gauge length is taken as the initial sample length, and it corresponds to a strain of 0%. Percent strain at any point in the test is defined as the change in length divided by the adjusted gauge length times 100%.

6(a). First cycle loading: Pull the sample to a strain of 50% at a constant cross head speed of 254 mm/min.

6(b). First cycle unloading: Hold the sample at 50% strain for 30 seconds and then return the crosshead to its starting position (0% strain) at a constant cross head speed of 254 mm/min. Hold the sample in the unstrained state for 1 minute.

6(c). Set from second cycle loading: Pull the sample at a constant cross head speed of 254 mm/min, till it reaches a load of 0.05 N/25.4 mm (0.020 N/cm). Record the extended gauge length ($l_{ext}$). Next, return the crosshead to its starting position (zero strain) at a constant cross head speed of 254 mm/min. Set is defined as the strain at a second cycle load of 0.05 N/25.4 mm (0.020 N/cm). Calculate % set as indicated below.

6(d). Second cycle unload: Next, return the crosshead to its starting position (zero strain) at a constant cross head speed of 254 mm/min.

Percent Set is defined as the percent strain at a second cycle load of 0.05 N/25.4 mm (0.020 N/cm). Calculate % set as indicated below.

A computer data system records the force exerted on the sample during the test as a function of applied strain. From the resulting data generated, the following quantities are reported (note that loads are reported as force divided by the width of the sample and do not take into account the thickness of the sample):

1. Loads at 25% strain and 50% strain (N/cm)
2. % set (Percent Strain measured at a second cycle load of 0.02N/cm);
3. % set=$(l_{ext}-l_{ini})/l_{ini}*100\%$.

Five repetitions are done on each sample and the average and standard deviation reported.

The Hysteresis Test can be suitably modified depending on the expected attributes and/or properties of the particular material sample to be measured. For example, the Test can be suitably modified where a sample of the length and width specified above are not available from the subject article.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A fastening member having a proximal region, a distal region ending at a distal end, and an intermediate region between the proximal region and the distal region, the fastening member being formed from a material web having a machine direction and a cross direction, comprising:
    a first layer formed of a first nonwoven web comprising first fibers, the first layer having first and second opposing sides, the first side having a surface area;
    wherein the proximal region includes a first portion of the first layer having a proximal region surface area that comprises a first portion of the surface area; and
    wherein the distal region includes a second portion of the first layer and has a distal region surface area that comprises a second portion of the surface area, the distal region also comprising a second layer formed of second nonwoven web comprising second fibers
    a third layer comprising an elastomeric film;
    a fourth layer comprising a third nonwoven web comprising third fibers;
    wherein the third layer is disposed between the first layer and the fourth layer and each of the first, third and fourth layers but not the second layer are present in the proximal region;
    wherein the second layer is disposed between the first layer and the fourth layer and each of the first, second and fourth layers but not the third layer are present in the distal region;
    wherein each of the first, second, third and fourth layers are present in the intermediate region;
    wherein the first, second and fourth layers are bonded together in the distal region at a plurality of bond sites arranged in a pattern, the bond sites comprising areas in which structures of the first, second and fourth layers are compressed together; and
    wherein the proximal region has a first tensile strength in the cross direction and the distal region has a second tensile strength in the cross direction, and the second tensile strength is greater than the first tensile strength;
    wherein the proximal region has a first stiffness and the distal region has a second stiffness, and the second stiffness is greater than the first stiffness; and
    wherein the first fibers, the second fibers and the third fibers are formed at least in part of polymers of like chemistry.

2. The fastening member of claim 1 wherein the first and second fibers are formed from a polymer selected from the group consisting of a polypropylene, a polyethylene and combinations thereof.

3. The fastening member of claim 2 wherein the first and second fibers comprise a polyethylene component.

4. The fastening member of claim 1 wherein at least one of the first and second fibers are multicomponent fibers having at least two component sections.

5. The fastening member of claim 4 wherein at least one of the first and second fibers have a polypropylene component and a polyethylene component.

6. The fastening member of claim 5 wherein the polyethylene component forms at least a portion of the external surfaces of the at least one of the first and second fibers.

7. The fastening member of claim 1, wherein the first and second fibers have a machine direction orientation.

8. The fastening member of claim 1 wherein the bond sites have shapes which form a substantially regular pattern.

9. The fastening member of claim 8, wherein the bond sites form shapes that have generally rounded profiles without macroscopically observable sharp corners.

10. The fastening member of claim 8, wherein the bond sites form shapes selected from the group consisting of circular shapes, oval shapes, ovaloid shapes, elliptical shapes, egg-shapes, "race-track"-shapes and combinations thereof.

11. The fastening member of claim 1 wherein at least a portion of the proximal region is activated.

12. A diaper comprising a wearer-facing, liquid permeable topsheet, an outward-facing, liquid impermeable backsheet, and an absorbent core disposed between the topsheet and the backsheet, the backsheet having a lateral front waist edge, a lateral rear waist edge, and a pair of longitudinal edges respectively joining the front waist edge and the rear waist edge, and a pair of fastening members as recited in claim 1, each fastening member respectively attached to the backsheet proximate to one of the respective longitudinal edges, with its proximal region relatively closer to the backsheet and its distal region relatively further from the backsheet.

* * * * *